United States Patent [19]

Beacham et al.

[11] 4,315,082
[45] Feb. 9, 1982

[54] PHOSPHORUS COMPOUNDS

[75] Inventors: Harry H. Beacham, Langhorne, Pa.; Robert D. Norris, Cranbury, N.J.

[73] Assignee: FMC Corporation, Philadelphia, Pa.

[21] Appl. No.: 61,138

[22] Filed: Jul. 26, 1979

Related U.S. Application Data

[63] Continuation of Ser. No. 866,493, Jan. 3, 1978, abandoned.

[51] Int. Cl.$^3$ ............... C08K 5/14; C08K 5/02
[52] U.S. Cl. ............... 525/20; 252/182; 252/188.3 R; 260/920; 260/934; 260/966; 521/907; 525/355; 526/231; 252/186
[58] Field of Search ............... 252/186, 182, 188.3 R; 260/DIG. 24, 920, 934, 966; 525/355, 20, 340; 521/907; 526/231

[56] References Cited

U.S. PATENT DOCUMENTS

| | | | |
|---|---|---|---|
| 2,960,526 | 11/1960 | Harrison et al. | 260/934 |
| 3,028,410 | 4/1962 | Zimmer | 260/968 |
| 3,338,864 | 8/1967 | Mageli et al. | 260/45.7 R |
| 3,420,786 | 1/1969 | Weber et al. | 260/45.7 R |
| 3,576,923 | 4/1971 | Randell et al. | 260/966 |
| 3,637,578 | 1/1972 | Wright et al. | 260/40 R |
| 3,639,506 | 2/1972 | Haaf | 260/23.7 M |
| 3,671,651 | 6/1972 | D'Angelo | 260/934 |
| 3,679,550 | 7/1972 | Orwell | 203/38 |
| 3,684,616 | 8/1972 | Wright et al. | 156/307.5 |
| 3,846,396 | 11/1974 | D'Angelo et al. | 525/20 |
| 3,859,395 | 1/1975 | Torhune | 260/966 |
| 3,882,203 | 5/1975 | Dulog et al. | 260/968 |
| 3,936,414 | 2/1976 | Wright et al. | 260/40 R |
| 3,994,856 | 11/1976 | Katchman | 260/42.47 |
| 4,055,714 | 10/1977 | Sheppard et al. | 260/934 |

OTHER PUBLICATIONS

"Peroxy Compounds", Ency. of Polymer Sci. and Tech., vol. 9, pp. 827–838, John Wiley, 1968.

*Primary Examiner*—Benjamin R. Padgett
*Assistant Examiner*—Irwin Gluck
*Attorney, Agent, or Firm*—Abner Sheffer; Frank Ianno; Eugene G. Seems

[57] ABSTRACT

Compositions comprising organic phosphorus compounds having a peroxygen group which is either a hydroperoxyalkyl (H—OO—C—) group or a peroxyether (—C—OO—C—) group. There is at least one such group per 500 phosphorus atoms in the composition. These peroxygen compounds may be made by passing oxygen through a liquid comprising a phosphorus compound which has an aliphatic carbon, having an abstractable hydrogen, directly attached to a carbon of an aryl ring; for example, an isopropylphenyl phosphate. The peroxygen compounds may be added to compositions comprising peroxide-reactive organic polymers to increase flame resistance.

11 Claims, 2 Drawing Figures

PHOSPHORUS COMPOUNDS

This is a continuation, of application Ser. No. 866,493, filed Jan. 3, 1978, now abandoned.

The invention relates to organic phosphorus compounds containing peroxygen group.

Organic phosphorus compounds, such as phosphates, are well known for use as flame retarding agents in organic plastics, either as the sole such agents or in combination with other ingredients such as halogen compounds. In such uses the phosphorus compound often also acts as a plasticizer.

One aspect of this invention relates to organic phosphorus peroxy compounds which are suitable as flame retarding agents and in which the peroxy group —O-O— is directly bonded on the one hand to an aliphatic carbon directly attached to an aromatic ring and on the other hand to (a) a hydrogen atom or (b) aliphatic carbon. In (a) the compound is a hydroperoxide in (b) it is a peroxyether Either or both types of groups may be present. Preferably the peroxy group (—OO—) is on a tertiary carbon atom (e.g. in a peroxyisopropylphenyl group of the formula The phosphorus-containing peroxy compounds of this invention have a flame retarding effect on plastics into which they are incorporated, owing in large part to their phosphorus content. They also have additional effects. For instance, they may increase the flame resistance (as compared to identical phosphorus compounds without the peroxy groups); see, for example, the data tabulated in Example 1 below. They may improve the flame resistance of plastics while reducing the often-undesirable decrease in glass transition temperature (Tg) that often results from incorporation of flame retardants; see, for example, the data tabulated in Example 5, below. Their use may increase the compatibility of the organic plastic with the organic phosphorus compound; see, for instance, the improvement in blooming characteristics noted in Example 7 below. They may act synergistically with flame retarding halogen compounds; see, for instance, the data in Example 6, below.

The phosphorus-containing peroxy compounds of this invention may also be used in place of other peroxy compounds such as those conventionally employed in the art as curing (crosslinking, vulcanizing) agents, polymerization catalysts or initiators for other free radical reactions such as grafting or synergism with halogen-containing flame retardants. In conventional processes of this type, the peroxy compound (such as dicumyl peroxide) forms low molecular weight decomposition products which are volatile, subject to migration and easily extracted. The resultant odor is objectionable and has been a major drawback in their use. In contrast decomposition of the peroxy compounds of this invention yields phosphorus-containing residues which are generally of relatively high molecular weight, less extractable, less volatile and less odorous. Furthermore, these phosphorus-containing residues are less likely to be flammable than the residues (such as hydrocarbons) from conventional peroxides. As noted above, their use may incorporate a phosphorus-containing residue directly into the chemical structure of the polymer.

In one preferred aspect of the invention, the phosphorus-containing peroxy compounds are formed, and used, in admixture with unperoxidized flame-retarding phosphorus compounds. Conveniently, a mixture of peroxidized and unperoxidized phosphorus compounds is formed by partially peroxidizing the phosphorus compound. Such a mixture may also contain molecules of varying peroxide contents, i.e., a mixture of molecules, some having one peroxy group per molecule and others having two or even three or more peroxy groups per molecule. Also there may be both hydroperoxy and peroxy ether groups in the mixture. One may carry out the peroxidation process to obtain a relatively high conversion to peroxy compounds (and concomitant formation of molecules having a plurality of peroxy groups) and then blend the resulting peroxy-rich mixture with more of the phosphorus-containing starting material or with another phosphorus-containing flame retardant compound. One may carry out the peroxidation process on a mixture of phosphorus compounds, one (or more) of which is resistant to peroxidation and one (or more) of which is more readily peroxidized. The peroxidation process may also be carried out in the presence of other compounds such as solvents or diluents (see Ex. 9 b below) or polymerizable monomeric or polymeric materials such as styrene, which may contain dispersed or dissolved polymeric materials such as unsaturated polyester resin (a relatively low polymer which copolymerizes with the styrene) or higher polymers such as diolefin polymers (e.g., rubbery polybutadiene-1,3, butadiene copolymers, etc.). In the peroxy-containing mixture, there is preferably at least one peroxyalkylaryl group per 500 phosphorus atoms, more preferably at least one such group per 100 P atoms (e.g. about 3, 5, 10, 20, 100, 200 or even 300 such groups per 100 P atoms) and the carbon:phosphorus atomic ratio is preferably less than about 100:1, a C:P ratio well below 50:1 (such as about 30:1 or less) being more preferred in order to provide a desirable level of phosphorus content for flame retardancy.

The following Examples are given to illustrate this invention further. In this application all proportions are by weight and all temperature are °C. unless otherwise indicated.

EXAMPLE 1

130 parts of a blend of styrene and ethylenically unsaturated polyester resins which are soluble in styrene and copolymerizable therewith is mixed with the following additives in the indicated amounts and then heat-cured in sealed glass tubes of ¼ inch diameter (at the temperatures indicated below) overnight (16 hours) after which the cured material is removed from its tube and its oxygen index is determined; in some cases, as indicated, the cured material, after removal from its tube, is given a post-cure in air at 100° C. overnight. Oxygen index is a measure of flame resistance (ASTM D2863).

The styrene-polyester resin solution is made by mixing 50 parts styrene, 50 parts Dion 6421 (a polyester of [a slight excess of] propylene glycol and a 1:1 [molar] mixture of maleic and isophthalic acid) and 30 parts Dow FR-1540 (a blend of 30% styrene and 70% of a polyester derived from maleic anhydride and dibromoneopentyl glycol).

The results are as follows:

| Additive and curing conditions | | Oxygen Index |
|---|---|---|
| (a) | 3 parts benzoyl peroxide; cured at 70° C. | 23 |
| (b) | 3 parts benzoyl peroxide plus 20 parts 4-isopropylphenyl diphenyl phosphate; cured at 70° C. | 25.7 |
| (c) | 20 parts of product made by treating 4-isopropylphenyl diphenyl phosphate with oxygen to form peroxyalkyl compound (as in Example 3 below); cured at 70° C. | 28.0 |
| (d) | 3 parts benzoyl peroxide plus 20 parts of phosphate ester of partially isopropylated phenol, made in the general manner described in Example 4a below; cured at 70° C. and then post-cured in air at 100° C. | 28.8 |
| (e) | 20 parts of product made by treating the phosphate named in d above with oxygen to form peroxyalkyl compound (as in Example 2a below); cured at 70° C. and post-cured in air at 100° C. | 29.9 |
| (f) | 10 parts of oxygen-treated material of Example 2a below | |
| | (i) cured at 70° C. | 29.6 |
| | (ii) cured at 110° C. | 33.5 |
| (g) | 3 parts benzoyl peroxide plus 30 parts tris (3-ethylpehnyl) phosphate | 27.4 |
| (h) | 30 parts of product made by treating tris (3-ethylphenyl) phosphate with oxygen to form peroxyalkyl compound (as in Example 2b below) | 31.3 |

These results indicate that the addition of the triaryl phosphates improves the flame resistance and that treating the phosphate ester to form peroxyalkylaryl phosphates prior to mixing with the polymerizable mixture gives an additional significant improvement.

In each of Examples 1a, 1b, 1d and 1g there is also present an amount of tricresyl phosphate equal to the amount of benzoyl peroxide, since the latter is, in each case, added in the form of 50:50 mixture with tricresyl phosphate, sold as "Luperco ATC paste."

EXAMPLE 2

(a) The additive used in Example 1e and f is prepared by passing oxygen through 20 g of the phosphate ester having dispersed therein 0.2 g of sodium formate and 10 mg of manganese naphthenate at about 125° C. The oxygen is bubbled through the material for about 8½ hours giving a product which, according to hydroperoxide titration (described below) contains about 28 hydroperoxyalkyl groups per 100 phosphorus atoms.

(b) The product used in Example 1h is made in a similar manner, in the presence of 1% sodium formate and 0.05% manganese naphthenate the oxygen being bubbled through for about 23 hours; the hydroperoxide titration indicates that there are about 20 hydroperoxyalkyl groups per 100 phosphorus atoms.

In view of these analyses for hydroperoxyalkyl content, it is quite probable, statistically, that the products of Example 2a and b contain triaryl phosphate molecules having two (or three) hydroperoxyalkyl groups per molecule together with triaryl phosphate molecules having only one hydroperoxyalkyl group and unchanged triaryl phosphate molecules.

EXAMPLE 3

The additive used in Example 1c is prepared by passing oxygen through 10 g of 4-isopropylphenyl diphenyl phosphate having dispersed therein 0.1 g of sodium formate and 10 mg manganese naphthenate at 125° C. The oxygen is bubbled through the material for about 57 hours giving a product which, according to hydroperoxide titration described below, contain about 60 hydroperoxyalkyl grups per 100 phosphorus atoms.

EXAMPLE 4

(a) Phenol is alkylated with propylene, in the manner described in U.S. Pat. No. 3,576,923, to produce a mixture having about 0.33 isopropyl groups per phenol (about 15 parts of propylene reacted, per 100 parts of phenol) and in which the ratio of o-isopropyl groups to m- and p-isopropyl groups is in the neighborhood of about 2:1. This mixture is then isomerized, in the manner described in U.S. Pat. No. 3,859,395 to change the o:m,p ratio (from its initial value of about 2:1) to about 1:2. The resulting isomerized alkylate is then esterified with $POCl_3$ (in the general manner described in U.S. Pat. No. 3,576,923) to produce a triaryl-phosphate which is purified by distillations at subatmospheric pressure. The presence of 0.33 isopropyl groups per phenol (in the alkylate) indicates that in the triaryl phosphate there are about 100 isopropyl groups per 100 phosphorus atoms.

(b) To the triarylphosphate of 4a there are added 0.5% sodium formate and 0.05% manganese naphthenate, and oxygen at substantially atmospheric pressure is then bubbled (from a capillary tube) through the phosphate maintained at about 125° C. for about 16 hours. As in the other Examples herein, the mixture is treated, by filtering or decanting after settling, to remove solids. Hydroperoxide titration indicates about 20-30 hydroperoxy groups per 100 phosphorus atoms, which indicates that a significant number (e.g. 70-80%) of the isopropyl groups of the triaryl phosphate are unreacted and that the product contains unoxidized original triarylphosphate molecules as well as triaryl phosphate molecules having one peroxyalkylaryl group; it is believed, on the basis of statistical probability, that there are also present triaryl phosphate molecules having two such peroxyalkylaryl groups and some triaryl phosphate molecules having three such groups. The product is a pale yellow oily liquid having a viscosity of about 42 centistokes at 100° F. Differential scanning calorimetry of its thermal decomposition shows a peak at about 230° C. (indicating that its peroxide content is largely hydroperoxide) with a shoulder in the neighborhood of about 200° C. (indicating the presence of peroxy ether groups, which have a lower decomposition temperature than the hydroperoxide groups).

EXAMPLE 5

This example relates to treatment of high impact polystyrene whose high impact properties are provided by modification of the polystyrene with a rubber; such materials are described for instance in U.S. Pat. No. 3,994,856. The polymer used in this Example is "DOW Styron 470 impact polystyrene" a polystyrene polybutadiene copolymer. The treatment is effected on a steam heated, differential speed two-roll compounding mill (135° C. front role, 120° C. back roll). First the high impact polystyrene is placed on the mill, forming a sheet on the hotter roll. Then there is added to the sheet, over a period of 10 minutes while milling continues, 10 parts of additive (as listed below) per 100 parts of polymer; the mixing is continued for another 10 minutes. During the entire period the hot material is exposed to the atmosphere. The material is then compression molded (between heated platens) into sheets 75 mils thick; the sheets are cut into strips for testing burning time and burning behavior according to UL-94 test method. The following results are obtained:

| Additive | Condition of hot material on mill at end of 20 minute mixing period | T g (°C.)* | Burning Time (secs)** |
|---|---|---|---|
| (a) None | Fluid (plastic) | 83 and 93 | 227 |
| (b) Unoxidized triaryl phosphate of Example 4a | More fluid than a but removable from mill | 65–67 | 80 |
| (c) Same as b plus 1 part cumene hydroperoxide per 100 parts of polymer | Less fluid than b | 70 | 90 |
| (d) Same as b plus 3 parts of cumene hydroperoxide per 100 parts of polymer | Slightly more than c | 62 | 123 |
| (e) Peroxidized phosphate of Example 4b | More fluid than a but less fluid than b | 75–77 | 81 |

*Tg is determined on a DuPont 900 Differential Thermal Analyzer.
**Burning time is in seconds (the sum of the burning times of 5 strips in the UL-94 test).

In the burning test all samples drip and ignite the cotton used in the test, but the behavior of e is a little better in this respect.

Differential scanning calorimetry (DSC) of the materials after milling indicates that very little or no peroxide remains; after molding, DSC shows no evidence of the presence of peroxide. All samples mold well and the molded sheets are tough as shown by the fact that they can be folded back on themselves without breaking.

In the working of the polymer on the heated mixing surfaces (i.e., the mill rolls) in this Example (and others below) heat is generated internally by the mixing forces so that any particular tiny zone within the material being mixed the temperature may rise, locally, to above the roll temperature; also, the hot mixing process occurs in the open air for an appreciable time, which may promote decomposition of a significant proportion of the peroxide without reaction of that portion of the peroxide (or radicals generated therefrom) with the polymer. This is also indicated by the fact that the product contains little if any residual peroxide. It will be understood that the mixing may be conducted under conditions in which these effects of the atmosphere and of mixing time are reduced, as in an inert (e.g., nitrogen) atmosphere or in a closed high speed mixing apparatus such as a screw extruder (in which the residence time may be about 1 to 2 minutes, for example) or a high torque sigma blade mixing apparatus, so that the mixed product may retain a significant proportion of the peroxide enabling the latter to act during or after, the shaping of the polymer to its final form.

EXAMPLE 6

This Example relates to treatment of moldable polyethylene. Using the two-roll compounding mill described in Example 5, but with both rolls at 132° C., low density high pressure polyethylene (density 0.924 g/cm$^3$, Union Carbide "DNB-0195 Natural7") is sheeted on the mill, with the gap adjusted to permit a small bead in the nip of the rolls. Then 6 parts of additive (as listed below) per 100 parts polyethylene are added slowly dropwise over a 20 minute period while milling continues. The materials are then compression molded at 160° C. into sheets 0.75 mm thick, which are tested for horizontal burning rate. The following results are obtained:

| Additive | Condition of hot material on mill | Horizontal Burning Rate (cm/in) | Burning Behavior |
|---|---|---|---|
| (a) None | Plastic (fluid) | 10.8 | Severe dripping |
| (b) Unoxidized triaryl phosphate | Becomes increasingly fluid and at end is too sticky to remove from mill hot. Removed by chilling rolls | 8.8 | Severe dripping |
| (c) Peroxidation product of phosphate of b | Appears to "gel" locally where drops of additive contact the polymer but then becomes uniform as milling continues. Easier to work on mill, and easier to strip off, than a | 7.6 | Moderate dripping |

In b the phosphate is a triarylphosphate of a highly isopropylated phenol, like that used in Example 10 g below: the peroxidation product used in c contains about 14 hydroperoxyalkyl groups per 100 P atoms (as measured by hydroperoxide tritration). Burning rate is measured according to ASTM D-635-72 flame test.

EXAMPLE 7

In a repetition of the milling and molding steps of Example 6 it is found that when the peroxidized phosphate is added the polyethylene begins to ball up on the mill (poor fluxing); good fluxing is obtained by then raising the roll temperature by about 5° C. It is also found that the molded product made with the peroxidized phosphate retains the additive to a markedly greater degree than the product made with the unoxidized phosphate; the latter product has a quite oily surface owing to marked phosphate migration to the surface ("blooming"). This indicates that aryl phosphate-containing radicals (such as a diphenylphosphatophenylalkyl radical) may be grafted to the polyethylene (which has pendent methyl groups) thus forming a modified polymer which has greater compatibility with the unreacted aryl phospate. The raising of the temperature needed for fluxing may indicate that a limited degree of cross linking of the polyethylene chains has occurred.

EXAMPLE 8

Ordinary general-purpose polystyrene (Union Carbide GP polystyrene) is mixed with additives on a mill as in Example 5, using a front roll temperature of 135° C. and a back roll temperature of 120° C., and then compression molded into sheets. The following tabulation gives the proportions of additives and the results.

| Additive | Proportions | | | | |
|---|---|---|---|---|---|
|  | a | b | c | d | e |
| Polystyrene | 100 | 100 | 100 | 100 | 100 |
| Peroxidized 4-isopropylphenyl diphenyl phosphate | 10 |  |  |  |  |
| "Di Cup R"(96% dicumyl peroxide) |  | 10 | 2 |  |  |
| Hexabromo-cyclo-dodecane | 10 | 10 | 10 |  | 10 |
| Tg (°C.) | 80,80 | 75,76 | 84,85 | 93,94 | 86,87 |
| Oxygen Index | 23.9 | 19.8 | 20.8 | 18.0 | 21.0 |

The peroxidized phosphate used in this Example contains (by hydroperoxide titration) about 20 hydroperoxyalkyl groups and (by peroxyether titrations) about 2.3 peroxyether groups per 100 phosphorus atoms.

EXAMPLE 9

(a) 22.7 grams of 4-isopropylphenyl diphenyl phosphate is mixed with 1.0 gram of sodium 2-ethylhexanoate. A stream of oxygen, from a capillary tube, is bubbled through the mixture, maintained at 125° C. for 118 hours. Iodometric titration of the product indicates 28% conversion to 4 ($\alpha$-hydroperoxy-$\alpha$-methylethylphenyl) diphenyl phosphate.

The crude reaction mixture is purified by column chromatography (silica gel; successive elution with benzene, chloroform and acetone) and the resulting purified hydroperoxy compound is tested as follows: NMR (CDCl$_3$) indicates 1.55 (s, 6H, CH$_3$), 7.13 (s, 14H, aromatic) and 5.93 (s, 1H, OOH). The infrared spectrum is nearly identical to that of the unoxidized starting material except that it contains the typical OH band (3300 cm$^{-1}$) for hydroperoxides (cumene hydroperoxide has an OH absorption at 3380 cm$^{-1}$). The elemental analysis, calculated for C$_{21}$H$_{21}$O$_6$P: C, 63.00; H, 5.29; found: C, 63.32; H, 5.45. The purified compound also tests positive for peroxide activity (starch iodide and acetic acid-isopropyl alcohol-sodium iodide). When tested by polarography it behaves similarly to cumene hydroperoxide ($-0.85$ volts vs. SLE for the subject hydroperoxide and $-1.1$ volts vs. SLE for cumene hydroperoxide).

(b) A mixture of 14.2 4-isopropylphenyl diphenyl phosphate, 40 ml xylene and 0.1 g sodium 2-ethylhexanoate is treated as in 9a with oxygen for 119 hours. At this stage the hydroperoxide titration indicates 42% conversion to hydroperoxide.

(c) A mixture of 50 grams of 4-isopropyl phenyl diphenyl phosphate and 0.5 g sodium formate is treated with oxygen as in 9a. At various stages hydroperoxide titrations indicate the following conversions to hydroperoxide: 28% in 58 hours; 55% in 70 hours. 71% in 72 hours.

(d) A mixture of 10 grams of 4-isopropylphenyl diphenyl phosphate, 0.1 g sodium formate and 5 mg manganese naphthenate is treated with oxygen as in 11a for 30 hours. Hydroperoxide titration at this stage indicates 60% conversion to the hydroperoxide. The DSC thermogram of a solution of 1% of the product in diallyl phthalate shows two peaks, one at about 230° C. indicating the presence (as in Example 9a) of hydroperoxide and the other at about 200° C. indicating the presence of peroxyether. In polarographic tests the material showed activity at $-0.85$ volts vs. SLE (as in Example 9a) as well as activity at $-1.75$ volts (representing the activity of the peroxyether); it should be noted that dicumyl peroxide, which is a peroxyether, similarly shows polarographic activity at a lower voltage than cumyl hydroperoxide, which is the corresponding hydroperoxide ($-2.05$ volts for dicumyl peroxide, $-1.1$ volts for cumene hydroperoxide) and that dicumyl peroxide similarly has its peak exotherm in diallyl phthalate at a lower temperature (182° C.) than cumyl hydroperoxide (205° C.).

Figure 1:
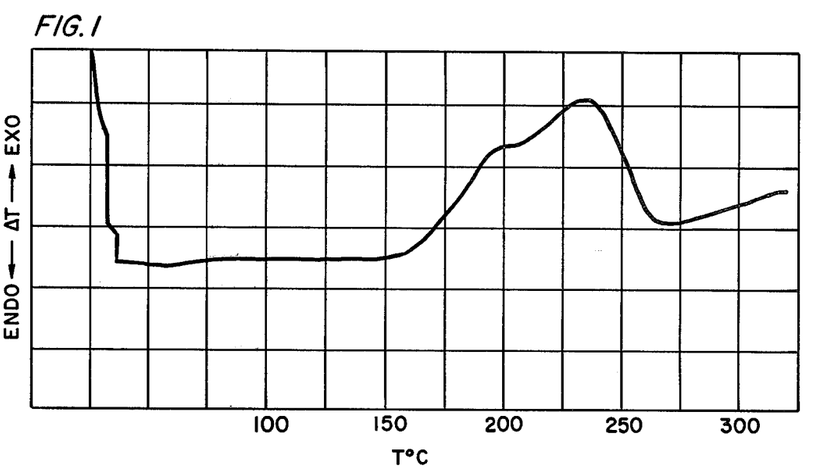
FIGS. 1 and 2 illustrate DSC thermograms of the products of examples 9d and 12e.

(e) Example 9d is repeated except that the duration of the oxygen treatment is shorter; titration indicates a 28% conversion to hydroperoxide. The DSC thermogram of a solution of 1% of the product in diallyl phthalate is shown in FIG. 1. It will be seen that it has two peaks as discussed in 9d.

(f) A triarylphosphate is prepared from a 70:30 mixture of 3-isopropylphenol and 4-isopropylphenol and is mixed with sodium formate and manganese naphthenate and then treated with oxygen as in 9a. After 30 hours the conversion to hydroperoxide (as indicated by hydroperoxide titration) is 52%. Since only 30% of the original isopropyl groups are 4-isopropyl this degree of conversion shows that the 3-isopropyl groups are also converted to hydroperoxide.

EXAMPLE 10

Phenol is alkylated with different amounts of propylene, in the general manner described in U.S. Pat. No. 3,576,923 to produce mixtures (of phenol and isopropylated phenols) having differing isopropyl contents, the isopropyl groups being largely in ortho position. The same, or similar, mixtures are then isomerized in the manner described in U.S. Pat. No. 3,859,395 to increase their content of m- and p-isopropyl groups. Each phenolisopropylated phenol mixture is then esterified with POCl$_3$ (in the general manner described in U.S. Pat. No. 3,576,923) to produce a triarylphosphate and each of these triaryl phosphates is then treated with oxygen in the general manner described in Example 4b for various periods. In each case hydroperoxide titration shows formation of hydroperoxides with the conversions being higher for the phosphates made from the isomerized alkylates. Some typical results are tabulated below:

| Approximate Isoproyl content (number of isopropyl groups per 100 phosphorous atoms) | Approximate Viscosity before peroxidation (centistokes at 100° F.) | Peroxide content (hydroperoxide group per 100 phosophorus atoms | Approximate Viscosity after peroxidation (centistokes at 100° F. |
|---|---|---|---|
| (a) 110 |  | 6 |  |
| (b) 110 isomerized | 20 | 28 | 42 |
| (c) 160 | 30 | 11 |  |
| (d) 160 isomerized | 30 | 37 | 67 |
| (e) 230 | 50 | 12 |  |
| (f) 280 isomerized | 50 | 65 | 550 |
| (g) 270 | 65 | 22 | 160 |

| Approximate Isoproyl content (number of isopropyl groups per 100 phosphorous atoms) | Approximate Viscosity before peroxidation (centistokes at 100° F.) | Peroxide content (hydroperoxide group per 100 phosphorus atoms) | Approximate Viscosity after peroxidation (centistokes at 100° F. |
|---|---|---|---|
| (h) 310 isomerized | 65 | 40 | |

Particularly in the case of the phosphates made from the more highly alkylated products, there is a significant proportion of molecules of phosphates having two or more isopropylphenyl groups (e.g., in the neighborhood of 80% by weight of such molecules in a phosphate made from an alkylated phenol having about 310 isopropyl groups per 100 phosphorus atoms and about 70% in a phosphate having about 280 isopropyl groups per 100 phosphorus atoms). The treatment with oxygen is believed to convert significant proportion of these molecules into molecules of triaryl phosphate having at least two peroxygen groups (e.g., hydroperoxyisopropyl groups) per molecule.

EXAMPLE 11

Tris(4-isopropylphenyl)phosphate is treated with oxygen at about 125° C. and the following conversions (indicated by hydroperoxide titration) are obtained after the following periods of treatment:

| | Period (hrs.) | Conversion (hydroperoyalkyl groups per 100 phosphorus atoms) of the tris (4-isopropylphenyl) phosphate |
|---|---|---|
| (a) contains 1% sodium octoate | 32 | 17 |
| (b) contains ½% sodium octoate | 31½ | 43 |
| (c) dissolved in a triaryl phosphate of a t-butylated phenol (0.33 t-butyl groups per phenol) and contains sodium formate and manganese naphthenate | 20 | 125 |

*10 g of the t-butyl phenyl phosphate, 5 g of the tris (4-isopropylphenyl) phosphate, 25 mg sodium formate, 8 drops manganese naphthenate.

In view of the oxidation resistance of the t-butylphenyl groups it is believed that little, if any, peroxidation of the solvent use in c occurs; this solvent is high boiling and is retained in the product. The high proportion of hydroperoxide indicates that the product c must have a relatively high content of triaryl phosphate molecules having two or three hydroperoxyalkyl groups per molecule. It is probable that such molecules are also present in a and b.

EXAMPLE 12

10 g of phosphate triester are sparged with oxygen at about 125° C. in the presence of sodium formate and manganese naphthenate; the following results are obtained:

| Alkylaryl phosphate | Period (hrs.) | Conversion (as in Example 11) |
|---|---|---|
| a. Tris cresyl phosphate in which the "cresyl" is largely (85%) m- and p-cresols, the balance being essentially ethyl phenols and xylenols | 12 | 8 |
| b. 2-ethylhexyl di (4-isopropylphenyl) phosphate | 4 | 41 |
| c. 2-chloroethyl di (4-isopropylphenyl) phosphate | 9 | 18 |
| d. tris (4-sec-butylphenyl) phosphate | 26 | 12 |
| e. n-butyl di (4-isopropylphenyl) phosphate | 20 | 31 |

Figure 2:
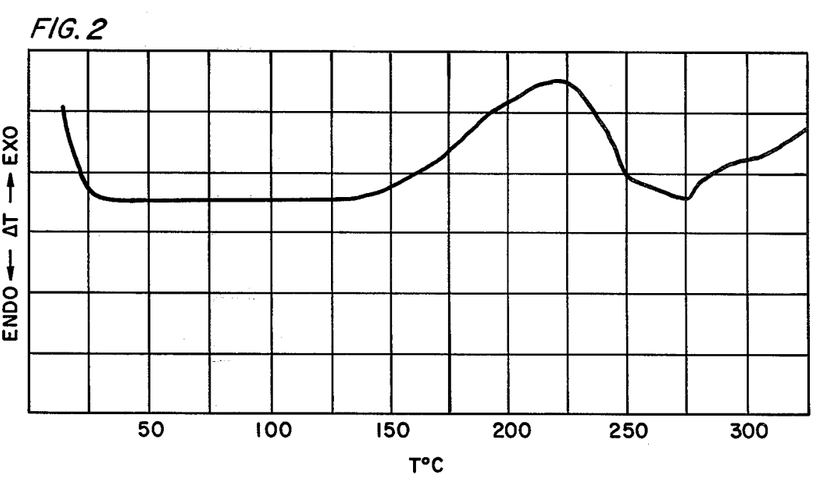

The proportions of sodium formate and manganese naphthenate, respectively employed in these runs are (a) 0.1 g and 10 mg, (b) 0.1 g and 5 mg, (c) 0.05 g and 5 mg, (d) 0.05 g and 5 mg, (e) 0.1 g and 5 mg. The DSC thermogram of a solution of 1% of the product of 12 e is shown in FIG. 2; it will be seen that it has a hydroperoxide peak at about 220° C. and a shoulder at a lower temperature, indicating the presence of peroxyether.

EXAMPLE 13

(a) Oxygen is bubbled through a mixture of 110 grams of 4-isopropylphenyl diphenyl phosphate, 0.6 g of sodium formate and 50 mg of manganese naphthenate for 5¾ hours; hydroperoxide titration indicates that there are about 37 hydroperoxyalkyl groups per 100 P atoms. After several months of storage at room temperature analysis by titration indicates that the hydroperoxyalkyl content is substantially unchanged and that there are about 10 peroxyether groups per 100 P atoms.

(b) Example 13 a is repeated, using, as the phosphate, an isopropylated phenyl phosphate like that used in Example 10g. After 4¾ hours of treatment the product is found (hydroperoxide titration) to contain about 17 hydroperoxyalkyl groups per 100 P atoms. After several months storage at room temperature analysis by titration indicates that there are about 12 hydroperoxyalkyl groups per 100 P atoms and substantially no peroxyether groups.

(c) Example 13 a is repeated, using, as the phosphate, an isomerized isopropylated phenyl phosphate like that used in Example 10b. After 11 hours of treatment the product is found (hydroperoxide titration) to contain about 26 hydroperoxyalkyl groups per 100 P atoms. After several months storage at room temperature analysis by titration indicates that there are about 25 hydroperoxyalkyl groups and about 3.4 peroxyether groups per 100 P atoms.

(d) Example 13a is repeated, using, as the phosphate, an isopropylated phenyl phosphate like that used in Example 10a (the amount of sodium formate is 1 g in this case). After 14 hours of treatment the product is found (hydroperoxide titration) to contain about 5 hydroperoxyalkyl groups per 100 P atoms. After several months storage at room temperature analysis by titration indicates that there are about 4.7 hydroperoxyalkyl and 0.7 peroxyether groups per 100 P atoms.

EXAMPLE 14

(a) A mixture of 20 grams of 4-isopropylphenyl diphenyl phosphate, 100 mg sodium formate and 10 mg manganese naphthenate is sparged with fine bubbles of oxygen fed through fritted glass. During the course of the reaction samples of the product are analyzed for hydroperoxyalkyl and peroxy ether groups, by titration as described below. The following results are obtained.

| Time (hrs.) | Hydroperoxyalkyl groups per 100 P atoms | Peroxyether groups per 100 P atoms |
| --- | --- | --- |
| 2 | 21.4 | 0 |
| 3 | 22.5 | 4.7 |
| 4 | 12.1 | 4.8 |

(b) A mixture of 110 grams of triaryl phosphate of isomerized isopropylated phenol (like that used in Example 10b), 0.6 g of sodium formate and 50 mg of manganese naphthenate is sparged with oxygen. After 2 hours treatment little, if any, hydroperoxyalkyl formation is noted (presumably due to antioxidant impurities in the sample) and an additional 50 mg of manganese naphthenate is added. Analysis, as in 14a, gives the following results:

| Time after addition of 2nd portion of manganese naphthenate (hrs.) | Hydroperoxyalkyl groups per 100 P atoms | Peroxyether groups per 100 P atoms |
| --- | --- | --- |
| 1½ | 3.7 | 2.5 |
| 2½ | 10.2 | 1.8 |
| 3½ | 14.9 | 4.0 |
| 4½ | 13.4 | 4.8 |

(c) A mixture of 110 grams of triaryl phosphate of highly isopropylated phenol (like that used in Example 10g), 0.6 g of sodium formate and 50 mg of manganese naphthenate is sparged with oxygen. Analysis as in 14a gives the following results:

| Time (hrs.) | Hydroperoxyalkyl groups per 100 P atoms | Peroxyether groups per 100 P atoms |
| --- | --- | --- |
| 1 | 7.9 | 0.8 |
| 3 | 14.8 | 5.2 |
| 4 | 17.6 | 2.3 |
| 5 | 12.7 | 10.7 |

(d) A mixture of 110 grams of triaryl phosphate of highly isopropylated phenol (like that used in Example 10g), 50 mg of sodium formate and 5 mg cobalt phthalocyanine is sparged with oxygen. After 1½ hours, little if any hydroperoxyalkyl formation is noted and an additional 500 mg of sodium formate and 50 mg of cobalt phthalocyanine are added. Analysis as in 14a gives the following results:

| Time after addition of 2nd portion of cobalt compound (hrs.) | Hydroperoxyalkyl groups per 100 P atoms | Peroxyether groups per 100 P atoms |
| --- | --- | --- |
| ½ | 7.2 | 1.5 |
| 3 | 13.0 | 12.1 |
| 4½ | 12.5 | 16.1 |

EXAMPLE 15

Oxygen is bubbled through a mixture of 10 g of an isopropylated phosphate like that used in Example 10g, 0.2 g of monosodium bis (4-isopropylphenyl) phosphate and 5 mg of manganese naphthenate for 5½ hours; hydroperoxide titration indicates that the product has 14 hydroperoxyalkyl groups per 100 P atoms.

EXAMPLE 16

A product made by oxygen-sparging an isomerized triaryl phosphate like that used in Example 10b in the presence of sodium formate and manganese naphthenate and having (by hydroperoxide titration) about 19 hydroperoxyalkyl groups per 100 P atoms is tested for stability by storing it at a temperature of about 25° C. for about 20 weeks in contact with a mass of (a) nickel wire, (b) stainless steel wire, (c) carbon steel wire. In each case the hydroperoxyalkyl content remains substantially unchanged.

Conventional techniques may be used for making the phosphorus compounds used as starting materials. In one procedure (to make the phosphates of Examples 8 and 9) diphenylphosphochloridate is reacted with 4-isopropylphenol (or 3-isopropylphenol or mixture of 4-isopropyl- and 3-isopropylphenol in Example 9e), as follows. To a stirred solution of 1 gram mole of isopropylphenol and 1.15 gram moles of triethylamine and 700 ml of methylene chloride in a nitrogen atmosphere, there is added drop-wise a solution of 1 gram mole of diphenylphosphorochloridate and 500 ml of methylene chloride. The temperature is maintained at 0°–10° C. during the addition which is complete in 1½ to 2 hours. The solution is then allowed to warm to room temperature and heated to reflux overnight. The cooled reaction mixture is slurried with 1 liter of distilled water and washed with 750 ml each of water, 5% aqueous sulfuric acid, 10% aqueous sodium carbonate and 10% aqueous sodium bicarbonate. The solution is dried over magnesium sulfate, filtered and concentrated (rotary evaporator). The crude product is flash distilled under vacuum with moderate care to remove the lower boiling fractions (phenols and chloridate) and then distilled under vacuum through a heated packed column for further purification.

The phosphates of Examples 12b and e may be produced by reacting one mole of the alcohol with a mole of $POCl_3$ and then reacting the product with the sodium salt of 4-isopropyl phenol. The phosphate of Example 12c may be produced by reacting ethylene oxide with di(4-isopropylphenyl) phosphochloridate.

The phenol alkylphenol mixtures produced by partial alkylation of phenol (as in Examples 4, 10, 11 and 13) are complex mixtures, containing di-alkylated as well as monoalkylated phenol molecules; see for instance Example 21 of U.S. Pat. No. 3,576,923, the discussion in U.S. Pat. No. 3,679,550 and the analyses in Example 1 of U.S. Pat. No. 3,859,395. Typical compositions of alkylates of the types used in Example 10 a,c,e, and g are:

| | Weight percent of component in | | | |
| --- | --- | --- | --- | --- |
| | a | c | e | g |
| Phenol | 60 | 39 | 22 | 14 |
| 2-isopropylphenol | 27 | 33 | 35 | 30 |
| 3- and 4-isopropylphenol | 11 | 14 | 16 | 19 |
| 2,6-diisopropylphenol | .2 | 4 | 7 | 5 |
| 2,4-diisopropylphenol | 1.6 | 7 | 12 | 16 |
| 2,5 and 3,5 diisopropylphenol | | 2 | 5 | 14 |
| 2,4,6 triisopropylphenol | | 1 | 3 | 2 |
| 2,3,5 triisopropylphenol | | tr | tr | tr |

On reaction of the alkylphenol-phenol mixture (as such or after isomerization) with POCl$_3$ there is formed a still more complex mixture containing triphenyl phosphate molecules, isopropylphenyldiphenyl phosphate molecules with isopropyl groups in various positions, di(isopropylphenyl)phenylphosphate molecules with isopropyl groups in various positions and tris(isopropylphenyl)phosphate molecules with isopropyl groups in various positions, as well as molecules containing one, two or even three diisopropylphenyl groups.

In the above Examples, dispersed Na salts (formate, octoate) settle out from the reaction mixture after agitation ceases and may be filtered off; Mn or Co compounds (when present) remain dissolved in the reaction mixture.

In the hydroperoxide titration mentioned above the sample is boiled with NaI in a weakly acidified alcohol solution to liberate iodine. The iodine is then titrated with sodium thiosulfate as a measure of total hydroperoxide content. Specifically, a 100 microliter (0.1 ml) aliquot of the sample is removed by a syringe and placed in a 125 ml Erlenmeyer flask. To this is added 10 ml of anhydrous isopropyl alcohol, 1 ml of acetic acid, and 10 ml of isopropyl alcohol saturated with sodium iodide. This mixture is refluxed for 10 minutes (at atmospheric pressure). If the aliquot being tested contains very little or no peroxide the solution remains colorless or turns a very pale yellow. With increasing peroxide concentration the color of the refluxed titration mixture is yellow, then orange, then brownish orange and sometimes reddish brown. After the mixture has been heated to reflux for 10 minutes, it is cooled to room temperature and 5–10 ml of water added. The solution is then titrated in conventional manner with 0.01 M sodium thio sulfate. The end point is arrived at when the solution turns from pale yellow to colorless. This is easily determined to within 1–2 drops. Each milliliter of 0.01 M sodium thio-sulfate used in the titration represents 0.005 gram mole of hydroperoxide groups. It is believed that this method does not indicate that total peroxide content or take into account the content of peroxyether groups.

In the peroxyether titration mentioned above the sample is refluxed in an inert atmosphere with acetic acid containing sodium iodide and a definite amount of water. Specifically of an aliquot of the sample is taken up in deoxygenated xylene (about 1.5 grams of sample per 50 ml xylene) and the resulting solution is added to deoxygenated acetic acid, after which 6 g NaI in 3 ml deoxygenated water are added and the mixture is refluxed under nitrogen for 30 minutes and then cooled under nitrogen, mixed with 100 ml of deoxygenated water, swirled to mix and titrated immediately with 0.1N sodium thiosulfate solution. A blank titration is also made to correct for interfering materials in the reagents. Further details as to the procedure are set forth in Hercules Inc. Di-Cup bulletin PRC-205B relating to iodometric assay methods for dicumyl peroxide; in the titrations yielding the peroxyether analyses described above, ground glass equipment equivalent to the flank arrangements described in that bulletin is used; also, the same 93% reaction factor is applied.

In the oxygenation process the time needed to attain a given content of hydroperoxide groups is influenced considerably by the degree of dispersion of the oxygen. A small tall body of liquid may undergo rapid reaction with oxygen supplied from a capillary tube, with the gas bubbles serving also to agitate the mixture. With a larger body, or a shallower one, mechanical stirring may be used to promote intimate contact. The use of fine bubbles of oxygen (such as can be supplied from a porous fritted-glass outlet) leads to faster results. Increase in the pressure under which the reaction is conducted (e.g., to 2 atmospheres gauge as compared to the atmospheric pressure at which the above Examples are conducted) also leads to faster results, presumably because more oxygen is dissolved in the reaction mixture. The oxygen fed to the reaction may be substantially pure oxygen or it may be in admixture with other materials which may be substantially inert in the reaction; e.g., air may be employed. The oxygen may be dry or may contain moisture; the inclusion of some moisture in the system (e.g., by partly saturating the oxygen with moisture) has been found to increase the rate of reaction (perhaps by promoting formation of a hydrated salt of the pro-oxidant or increasing its tendency to dissolve) but too high a moisture content appears to inhibit the increase in the desired peroxide content during reaction.

In a preferred embodiment of the process an acid acceptor such as a weak base is present (e.g., in about 0.1 to 5% concentration, preferably about 0.5 or 1%) during the treatment with oxygen. It is believed that this serves to neutralize acidity present, or formed, in the reaction mixture. Particularly good results have been obtained with a dispersed sodium salt of a relatively strong carboxylic acid, such as sodium formate which is usually substantially insoluble in the organic phosphorus compound being treated; sodium formate is known to form aqueous solutions of pH about 7 and to have a buffering action. Other salts, such as sodium octoate (e.g., 2-ethylhexoate), sodium oleate and sodium aryl phosphate (as in Example 15) have also been found to be effective. It is possible that sodium aryl phosphates or sodium salts of the weakly acidic hydroperoxides, or both, are formed in the reaction mixture when other sodium salts (e.g., sodium formate) are used as the antacids; in an analysis of a filtered product having about 13 hydroperoxyalkyl groups per 100 P atoms, made from a highly isopropylated triaryl phosphate like that used in Example 10g, it is found that the acid number is about 1.6 mg KOH per gram and the sodium content is in the neighborhood of 500 ppm.

The peroxidation reaction may be speeded up by including a small amount of a pro-oxidant, such as suitable transition metal pro-oxidant compound, preferably soluble in the phosphorus compound. Good results are obtained with such compounds as manganese naphthanate (e.g. a salt which, as in the above Examples, contains about 6% Mn), manganese phthalocyanine, and cobalt phthalocyanine in an effective metal concentration of say, in the range of about 0.0005 to 0.05% such as about 0.003 or 0.006%). It is found that the pro-oxidant reduces the induction period without causing rapid decomposition of the resulting peroxide. As shown in the Examples above, the pro-oxidant may be permitted to remain in he peroxidized mixture in use and no special separation steps are needed. At times the phosphate being treated may contain antioxidant compounds (antioxidant effects may be possibly due, for instance, to significant concentrations of lower-boiling impurities such as unesterified or partially esterified reactants used to make the phosphate triester) in which case it may be desirable to add a further quantity of prooxidant in order to start a more rapid peroxidation reaction (as can be seen in Examples 14b and d).

The peroxidation reaction may be effected at room temperature but it is preferable, particularly in the initial stages of the reaction, to use elevated temperatures, such as within the range of about 100° to 150° C., more preferably about 120° to 130° C. The reaction may be effected at a series of temperatures, such as an initial higher temperature (e.g., above about 120° C., e.g., 125° or 130° C. or higher) to minimize the induction period and then a lower temperature (e.g., below about 120° C. such as 115, 110 or 100° C. or lower).

The preferred peroxides are those made from compounds having benzylic hydrogen (i.e. compounds having an aliphatic carbon having an abstractable hydrogen and directly attached to a carbon of an aryl ring), the peroxide thus being formed by a process involving abstraction of that hydrogen and its replacement with an —OO— group. While (as shown by Examples 12a and 2b above) that carbon atom may carry two or one additional hydrogen atoms, best results are obtained when the ring-attached carbon atom is a secondary carbon attached to two other carbon atoms, as when it is part of an isopropyl or secbutyl radical. It is believed that t-butyl radicals, such as are present in Example 11c above, are resistant to peroxide formation so that the t-butylated triaryl phosphate of that Example serves as a substantially inert solvent in the reaction as well as a flame resistant component (e.g. plasticizer) in the organic plastic to which the mixture is added. It is believed that molecules of ortho-isopropylated phenyl phosphates, such as 2-isopropylphenyl diphenyl phosphate (present, for instance, in relatively large proportions in the phosphate used in Examples 10 and 13d) serve a similar function; it appears that there may be steric hindrance, owing to proximity to the phosphorous-oxy portion of the molecule, that makes the o-isopropyl substituent resistant to peroxidation. It is preferred that the peroxidizable alkyl substituent be relatively small, e.g. containing less than nine carbon atoms (more preferably less than six carbons), but it is within the broader scope of the invention to employ longer substituents such as those having twelve or eighteen carbon atoms. The substituent is preferably saturated hydrocarbon but it may carry substituents such as Cl, F, ester (e.g., CH$_3$COO—), amide (e.g., NH$_2$CO—) or aryl (e.g. phenyl). The aromatic ring is preferably a benzene ring and it may have substituents such as Cl, F, other alkyl (e.g. t-butyl), chloroalkyl, fluoroalkyl, aryl (e.g., phenyl), aralkyl (e.g., benzyl); it may be a condensed ring (e.g., a naphthalene ring).

As illustrated in the above Examples, the phosphorous compounds to be peroxidized may be phosphates, such as triaryl phosphates (which are preferred), monoalkyl diaryl phosphates (including, of course, compounds having substituents on the alkyl group as in Example 12c) or dialkyl monoaryl phosphates. They may also be phosphonates having an aliphatic-substituted aryl group which is directly attached to the P atom or is attached to the P atom through oxygen or both, for instance, it may be di (p-isopropylphenyl) ester of p-isopropylphenyl-phosphonic acid, or another ester (e.g., aryl, alkyl [including cycloalkyl] esters) of an isopropylphenylphosphoric acid such as the methyl phenyl, dimethyl or diphenyl or isopropyl (p-isopropylphenyl) ester of p-isopropylphenyl phosphonic acid, or it may be di (4-isopropylphenyl) ester of methylphosphonic acid (or of phenylphosphonic acid) or another ester (e.g., a mixed ester such as mixed 4-isopropylphenyl phenyl ester or mixed 4-isopropylphenyl methyl ester) of such a phosphonic acid. Other substituents may be present as discussed above.

It is also within the broader scope of the invention to use, as the phosphorus compound having the peroxidizable alkylaryl group, a phosphine oxide or a phosphinate, e.g. tri (4-isopropylphenyl) phosphine oxide or dimethyl 4-isopropylphenyl phosphine oxide. As with the other phosphorus compounds, these may peroxidized while dissolved in a solvent, which may be substantially inert (as described above) or may be another peroxidizable alkylaryl phosphorus compound, such as a phosphate.

The compounds (such as phosphates and phosphonates) may be esters of polyhydric alcohols or polyhydric phenols, such as the mixed ester of phosphoric acid with propanediol-1,3 and 4-isopropylphenol (e.g. having the formula where R represents the carbon chain portion of polyhydric alcohol). It will be understood that such compounds may have a plurality of phosphorus atoms, e.g. the mixed phosphate ester of pentaerythritol and isopropylphenol having the type formula or the mixed phosphate ester of bis-phenol A and isopropylphenol having the type formula in which R may be aliphatic (including cycloaliphatic) such as methyl, butyl or octyl or aromatic (such as phenyl or isopropylphenyl).

It is also within the broader scope of the invention to use, as the phosphorus compound having the peroxidizable alkylaryl group, a phosphazene, such as an alkylaryloxyphosphazene, e.g. a reaction product of sodium isopropylphenoxide and hexachlorocyclotriphosphazene.

It will be understood, of course, that the composition should be substantially free of amounts of active peroxide-destabilizing groups which would destroy the peroxide groups by reaction therewith or by catalytic action. For instance, the presence of unneutralized or unbuffered active acidic groups (or groups in the presence of moisture which would form such strongly acidic groups) could prevent formation of the desired peroxide content or act to destroy already formed peroxide; also the presence of certain reducing agents (e.g. phosphites) or amines, or certain concentrations of metal contaminants could act to destabilize the peroxides. The preferred compositions are sufficiently free of such destabilizing materials that on storage (e.g. for at least 1 day at 27° C. and, as indicated in Examples 13 and 16, preferably for well over a week, such as a month or more at room temperature) they lose less than ⅓ of their peroxide content; more preferably there is substantially no loss on such storage.

We believe that when isopropylphenyl phosphates of the type used as plasticizers or hydraulic fluids are exposed to oxidizing conditions, in such use, traces of hydroperoxyl-alkylphenyl phosphates may be formed initially and that these break down quickly under such oxidizing conditions, possibly owing to the presence of sufficient quantities of unbuffered acidic species (e.g. hydrolysis products having groups). The following Example describes an oxidation in the absence of a buffering agent in the presence of a pro-oxidant.

EXAMPLE 17

Oxygen is bubbled through a mixture of 42 g of a triarylphosphate of a highly isopropylated phenol (like that used in Example 10 g above) and 28 mg of manganese naphthenate at 120°–125° C. for 20 hours. The reaction mixture turns a dark reddish-brown; hydroperoxide titration of this mixture indicates that no peroxide is present (the titration is carried out under such conditions that a positive result would be obtained if 2 hydroperoxide groups per 1000 phosphorus atoms were present).

As mentioned above, organic peroxides have been used as cross-linking agents, polymerization catalysts, grafting agents and halogen synergists with a wide variety of polymers. The uses of peroxides are discussed, for instance, in the article on Peroxy compounds in the Encyclopedia of Polymer Science and Technology Vol. 9, pages 827–838 (published by Interscience) and the peroxy compounds of this invention may be employed in those uses, with the various types of polymers named in that article. The peroxy compounds of this invention may be employed as the peroxides in the compositions described in U.S. Pat. Nos. 3,637,578, 3,936,414, and 3,684,616. Among the halogen compounds with which the peroxy compounds of this invention may be used as synergists are those named in U.S. Pat. Nos. 3,338,864 and 3,420,786.

As mentioned earlier, organophosphorous compounds have been conventionally employed as flame retarding additives, e.g. plasticizers, in organic polymers such as polyvinyl chloride, phenol-formaldehyde resins, nylons, acrylic resins, polystyrene, aminoplasts such as melamineformaldehyde resins, polyolefins (e.g. polyethylene, polypropylene), polyurethane foams, other elastomers such as neoprene, cellulose esters (e.g. cellulose acetate or acetate butyrate) and engineering plastics (e.g. polyphenylene oxide such as described in U.S. Pat. No. 3,639,506). The peroxy compounds and mixtures of this invention may be used in the same way. They may be similarly included in other polymers such as polycarbonates (e.g. the Lexan resins, polycarbonates of bis-phenol A) or ABS polymers (acrylonitrile-butadiene-styrene copolymers, including block and graft copolymers).

The proportions of the peroxy-containing phosphorus compounds will depend, of course, on the intended use and will generally be more than 0.1% and less than 50% of the weight of the polymer.

The conditions used for obtaining the thermograms of FIGS. 1 and 2 are as follows: The instrument used is a Dupont 900 Differential Thermal Analyzer set at: T; 50° C./inch, ΔT; 0.5° C./inch, and Rate 20° C./minute. Sample sizes are 5–10 mg.

Pursuant to the requirements of the patent statutes, the principle of this invention has been explained and exemplified in a manner so that it can be readily practiced by those skilled in the art, such exemplification including what is considered to represent the best embodiments of the invention. However, it should be clearly understood that, within the scope of the appended claims, the invention may be practiced by those skilled in the art, and having the benefit of this disclosure, otherwise than as specifically described and exemplified herein.

We claim:

1. A mixture of a peroxide-reactive polymer and a peroxide composition,
    said peroxide composition comprising an organic phosphorus compound having a hydroperoxide group attached directly to a carbon atom of said organic phosphorus compound, there being at least one such hydroperoxide group per 500 phosphorus atoms in said composition.

2. A mixture as in claim 1 containing a bromine compound.

3. A mixture of a flammable polymeric plastic, a bromine compound and a peroxy-containing composition, said bromine compound acting synergistically with peroxide to improve the flame resistance of said plastic,
    said peroxide composition comprising an organic phosphorus compound having a peroxygen group, said peroxygen group being a hydroperoxide group attached directly to a carbon atom of said organic phosphorus compound or being a peroxy-ether group attached directly to two carbon atoms of said organic phosphorus compound, there being at least one such peroxygen group per 500 phosphorus atoms in said composition.

4. Process which comprises mixing a peroxide-reactive moldable polymer with a peroxide composition, said peroxide composition comprising an organic phosphorus compound having a hydroperoxide group attached directly to a carbon atom of said organic phosphorus compound, there being at least one such hydroperoxide group per 500 phosphorus atoms in said composition.

5. Process as in claim 4 in which said moldable polymer comprises a peroxide-crosslinkable elastomeric diolefin polymer.

6. Process as in claim 4 in which said moldable polymer comprises polystyrene.

7. Process as in claim 4 in which said moldable polymer comprises styrene and an unsaturated polyester copolymerizable therewith.

8. Process as in claim 4 in which said moldable polymer comprises a polyolefin.

9. Process as in claim 8 in which said moldable polymer comprises polyethylene.

10. A mixture as in claim 1 in which said phosphorus compound has a peroxyisopropylphenyl group.

11. A composition as in claim 10 in which said phosphorus compound is a peroxyisopropylphenyl phosphate.

* * * * *